United States Patent [19]

Naumann et al.

[11] 4,047,923
[45] Sept. 13, 1977

[54] HETEROCYCLIC SULFONIUM SALT CONTAINING PLANT-GROWTH REGULANT COMPOSITIONS

[75] Inventors: Klaus Naumann, Cologne; Klaus Lurssen, Grosskoenigsdorf; Klaus Sasse, Schildgen, all of Germany

[73] Assignee: Bayer Aktiengesellschaft, Leverkusen, Germany

[21] Appl. No.: 588,083

[22] Filed: June 18, 1975

Related U.S. Application Data

[62] Division of Ser. No. 476,760, June 5, 1974.

[30] Foreign Application Priority Data

June 19, 1973 Germany .............................. 2331185

[51] Int. Cl.² .............................................. A01N 5/00
[52] U.S. Cl. .............................................. 71/76; 71/90;
260/327 P; 544/59
[58] Field of Search ................... 71/76, 90; 260/243 B

[56] References Cited

U.S. PATENT DOCUMENTS

| | | | |
|---|---|---|---|
| 3,321,295 | 5/1967 | Newallis et al. ........................... 71/88 |
| 3,402,039 | 9/1968 | Mussell et al. ............................ 71/76 |
| 3,652,255 | 3/1972 | Osieka et al. ............................. 71/76 |
| 3,828,036 | 8/1974 | Quinlan ............................. 260/243 B |
| 3,856,501 | 12/1974 | Zeeh et al. ................................. 71/90 |
| 3,905,798 | 9/1975 | Zeeh et al. ................................. 71/76 |
| 3,913,436 | 5/1974 | Duerr et al. ....................... 260/243 B |

*Primary Examiner*—Glennon H. Hollrah
*Attorney, Agent, or Firm*—Burgess, Dinklage & Sprung

[57] ABSTRACT

Plant-growth regulating compositions and methods having strong effects on plant growth, containing a heterocyclic sulfonium salt of the formula

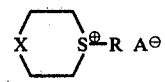

(I)

in which
R is alkyl; substituted alkyl; alkenyl; alkynyl; cycloalkyl; or aralkyl which is optionally substituted in the aryl moiety;
$A^-$ is one equivalent of an anion; and X is oxygen or the group $N+R'R''$ $A^-$ or $S+-R'''$ $A^-$ in which $A^-$ is identified as above;
R' and R", which may be identical or different, are each alkyl of up to 6 carbon atoms; and
R''' is defined as R or can be, together with R, an ethylene linkage.

9 Claims, No Drawings

HETEROCYCLIC SULFONIUM SALT CONTAINING PLANT-GROWTH REGULANT COMPOSITIONS

This is a division of application Ser. No. 476,760, filed June 5, 1974.

The present invention relates to plant-growth regulant compositions and to methods for regulating plant growth. More specifically, the invention relates to such compositions containing, and methods employing, certain heterocyclic sulfonium salts.

It is known that certain 2-halogenoethyl-trialkylammonium salts, especially (2-chloroethyl)-trimethylammonium chloride, display plant-growth-regulating properties (see U.S. Pat. No. 3,156,544). However, the action of these compounds is not always satisfactory, especially if low amounts and concentrations are used.

It has been found that the heterocyclic sulfonium salts of the following formula display strong plant-growth-regulating properties:

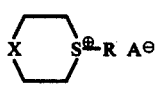

(I)

in which
R is alkyl; substituted alkyl; alkenyl; alkynyl; cycloalkyl; or aralkyl which is optionally substituted in the aryl moiety;
$A^-$ is one equivalent of an anion; and
X is oxygen or the group $N^\oplus R'R''$ $A^\ominus$ or $S^\oplus$-R''' $A^\ominus$ in which
$A^\ominus$ is identified as above;
R' and R'', which may be identical or different, are each alkyl of up to 6 carbon atoms; and
R''' is selected from alkyl; substituted alkyl; alkenyl; alkynyl; cycloalkyl; or aralkyl which is optionally substituted in the aryl moiety; or
R''', conjointly with R, forms the group —CH$_2$—CH$_2$—.

The present invention thus provides a plant-growth-regulating composition containing as active ingredient a compound of the formula (I) above in admixture with a solid or liquefied gaseous diluent or carrier or in admixture with a liquid diluent or carrier containing a surface-active agent.

The present invention also provides a method of regulating the growth of plants, which comprises applying to the plants or a plant habitat a compound of the formula (I) above alone or in the form of a composition containing as active ingredient a compound of the formula (I) above in admixture with a diluent or carrier.

Surprisingly, the heterocyclic sulfonium salts to be used according to the invention display a substantially greater plant-growth-regulating action than the known compound (2-chloroethyl)-trimethylammonium chloride, which is chemically the nearest active compound of the same type of action. The invention thus represents a valuable enrichment of the art.

Preferably, R is an optionally substituted straight-chain or branched alkyl of from 1 to 4 carbon atoms (preferred substituents being hydroxyl, methoxy, methylcarbonyl, alkoxycarbonyl of from 1 to 4 carbon atoms in the alkyl moiety and halogen, especially chlorine and bromine), alkenyl of from 2 to 4 carbon atoms, alkynyl of from 2 to 4 carbon atoms, cycloalkyl of from 3 to 12 carbon atoms, especially 3 to 7 carbon atoms, and aralkyl of from 1 to 4 carbon atoms in the alkyl moiety and 6 to 10 carbon atoms in the aryl moiety, the aryl moiety optionally being substituted by halogen, for example chlorine; $A^\ominus$ is halide, especially chloride, bromide or iodide, tetrafluoborate, or alkylsulfate, especially methylsulfate or ethylsulfate; X is oxygen or an $N^\oplus R'R''$ $A^\ominus$ group, in which R' and R'' are each alkyl of from 1 to 4 carbon atoms and $A^\ominus$ is one of the anions mentioned above, or a $S^\oplus$—R''' $A^\ominus$ group, in which R''' is one of the aforesaid preferred radicals specified for R or, conjointly with R, forms the group —CH$_2$CH$_2$—.

The flowing may be mentioned as examples of the active compounds which can be used according to the invention: 1,4-dimethylsulfonia-cyclohexane dimethosulfate, 1,4-diethylsulfonia-cyclohexane difluoborate, 1,4-diethylsulfonia-cyclohexane diethosulfate, 1,4-dipropylsulfonia-cyclohexane dibromide, 1,4-dibenzylsulfonia-cyclohexane dichloride, 1,4-dicyclopentylsulfonia-cyclohexane diiodide, 1,4-di-(β-chloroethyl)-sulfoniacyclohexane dichloride, 1,4-divinylsulfonia-cyclohexane dichloride, 1,4-dipropargylsulfonia-cyclohexane dibromide, 1,4-disulfonia-bicyclo-(2,2,2)-octane dibromide, 1-methylsulfonia-4-oxacyclohexane chloride, 1methylsulfonia-4-oxacyclohexane methosulfate, 1-benzylsulfonia-4-oxacyclohexane chloride and 1-methylsulfonia-4-dimethylammonia-cyclohexane dimethosulfate.

The compounds which can be used according to the invention are in some cases known (see Berichte 19, 696-702 (1886); Berichte 67, 1142-1144 (1934); and J. Org. Chem. 11, 704-718 (1946)). However, their use for regulating plant growth has not previously been described.

Some of the compounds according to the invention are new but can be prepared in a simple manner in accordance with conventional processes. They are obtained, for example, when cyclic sulfur compounds of the formula

(II)

in which
Y is oxygen, sulfur or the NR' grouping wherein
R' is alkyl of from 1 to 6 carbon atoms,
are reacted with compounds of the formula $$R^{IV} - Z \qquad (III)$$

in which
$R^{IV}$ is optionally substituted alkyl, alkenyl, alkynyl, cycloalkyl, aralkyl which is optionally substituted in the aryl moiety, or the triethyloxonium ion, and
Z is halogen, alkylsulfate or tetrafluoborate, optionally in the presence of a solvent, at temperatures between 0° C and 130° C.

The compounds of the formula (II) used as starting materials are known or can be prepared according to known processes (see J. Chem. Soc. 119, 1249-1256; and Synth. 2, (4), 183 (1970)). 1,4-dithiane, 4-oxathiacyclohexane and N-methylthiomorpholine may be mentioned as examples of compounds of the formula (II).

The compounds of the formula (III) also required as starting materials are also known. The following may be mentioned as examples thereof; methyl iodide, ethyl bromide, propyl chloride, allyl chloride, propargyl chloride, benzyl chloride, 4-chlorobenzyl chloride, 2,4-dichlorobenzyl chloride, chloroacetone, chloroacetic acid and its esters, chloromethyl ether, chloromethylnaphthalene, dimethyl sulfate, diethyl sulfate and triethyloxonium tetrafluoborate. acetone, chloroacetic acid and its esters, chloromethyl ether, chloromethylnaphthalene, dimethyl sulfate, diethyl sulfate and triethyloxonium tetrafluoborate.

Solvents used in the reaction described above are preferably lower alcohols, for example methanol, and chlorinated hydrocarbons, such as methylene chloride and chloroform, as well as dimethylformamide, acetonitrile, acetone, dioxane or water.

In the preparation by the above process, of the compounds to be used according to the invention, the reaction products are either obtained directly in a crystalline form after completion of the reaction or can, after completion of the reaction, be separated out in an oily or crystalline state by addition of a solvent in which they are insoluble. The crystalline products are isolated — if necessary after prior concentration of the reaction mixture— by simple filtration. Additional purification can be achieved by reprecipitation.

If the reaction products are obtained as oils, they are isolated by first separating the phases and then purifying the oil by treatment with active charcoal in aqueous or alcoholic solution.

In the compounds which can be prepared according to the above process it is possible, if $Y^-$ represents chloride, bromide or iodide, to exchange the anion by reaction with a silver salt. Furthermore, the anion can be exchanged by using an anion exchange resin.

1,4-Disulfonia-bicyclo-(2,2,2)-octane dibromide can not only be prepared by the process described in the literature (see J. Org. Chem. 11, 704-718 (1946)) but also by treating tris-2- hydroxyethyl-sulfonium chloride with aqueous hydrobromic acid at temperatures between 100° C and 140° C. THe product is suitably isolated by concentrating the reaction mixture under reduced pressure and freeing from impurities the crystalline residue which remains by washing it with methanol. Tris-2-hydroxyethylsulfonium chloride, required as a starting material, is already known (see J. Chem. Soc. 1931, 224–236).

The preparation of the compounds to be used according to the invention is illustrated in the following Examples.

EXAMPLE 1

Preparation of 1,4-diethylsulfonia-cyclohexane ditetrafluoborate

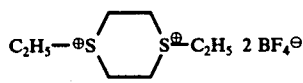

(1)

36.4 g (0.2 mole) of triethyloxonium tetrafluoborate were added to a solution os 12.0 g (0.1 mole) of 1,4-dithiane in 300 ml of methylene chloride at 20° C and the mixture was left to stand for several hours at room temperature. The solid which had separated out was then filtered off and was recrystallized from methanol for further purification. 29.9 g (85% of theory) of 1,4-diethylsulfonia-cyclohexane ditetrafluoborate of melting point 140° C were obtained.

Analysis.

Calculated: for $C_8H_{18}F_8B_2S_2$, 27.3% C, 5.2% H, 18.2%. S.

Found: 27.4% C, 5.3% H, 18.3% S.

EXAMPLE 2

Preparation of 1-methylsulfonia-4-oxacyclo-hexane iodide

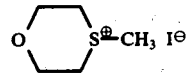

(2)

71 g (0.5 mole) of methyl iodide were added to a solution of 52 g (0.5 mole) of 4-oxa-thiacyclo-hexane in 50 ml of acetonitrile and the mixture was heated to 50° C for 2 hours. After it had cooled, 100 ml of ether were stirred into the reaction solution and the product which hereupon separated out was isolated. 73.8 g (60% of theory) of colorless 1-methylsulfonia-4-oxacyclo-hexane iodide of melting point 188° C were obtained.

Analysis.

Calculated: For $C_5H_{12}IOS$, 24.4% C, 4.5% H, 51.6% I.

Found: 24.6% C, 4.3% H, 51.9% I.

EXAMPLE 3

Preparation of 1-methylsulfonia-4-dimethylammoniacyclohexane dimethosulfate

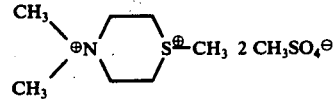

(3)

63 g (0.5 mole) of dimethyl sulfate were added to a solution of 23.4 g (0.2 mole) of N-methyl-morpholine in 150 ml of dimethylformamide and the mixture was heated to 130° C for ten hours. After cooling to room temperature, 200 ml of ether were stirred into the reaction solution and the oil which hereupon separated out was isolated. 61 g (83% of theory) of 1-methylsulfonia-4-dimethylammonia-cyclohexane dimethosulfate were obtained in the form of a viscous oil.

Analysis.

Calculated: for $C_9H_{23}NO_8S_3$, 5.2% N, 36.0% S.

Found: 5.8% N, 35.8 S.

EXAMPLE 4

Preparation of 1,4-disulfonia-bicyclo-(2,2,2)octane dibromide

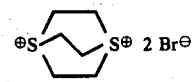

(4)

A mixture of 202.5 g (1mole) of tris-2-hydroxyethyl-sulfonium chloride and 600 ml of 48% strength hydrobromic acid was heated to 120° C for 4 hours. During the reaction, a mixture of 1,2-dibromoethane, 1,4-dithiane and water distilled off. After subsequent cooling, the reaction mixture was concentrated in vacuo and the residue which remained was freed from adhering impurities by washing it with methanol. 119.5 g (72% of theory) of 1,4-disulfonia-bicyclo-(2,2,2)-octane dibromide of melting point 193° C (decomposition) were obtained.

Analysis.
Calculated: for $C_6H_{12}Br_2S_2$, 23.4% C, 3.9% H.
Found: 23.4% C, 3.9% H.

EXAMPLE 5

Preparation of 1-methyl-sulfonia-4-dimethylammoniacyclohexane dichloride

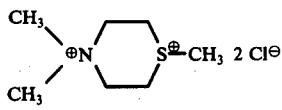 (5)

An aqueous solution of 1-methylsulfonia-4-dimethylammonia-cyclohexane dimetho-sulfate was filtered over a column containing an anion exchange resin charged with chloride ions. After evaporation of the eluate under reduced pressure 1-methylsulfonia-4-dimethylammonia-cyclohexane dichloride was isolated in form of hygroscopic crystals.

Analysis.
Calculated: for $C_7H_{17}NS\ Cl_2$, 38.5% C, 7.8% H, 6.4% N, 14.7% S. Found: 38.9% C, 7.7% H, 6.4% N, 15.2% S.

NMR-data (Solvent: $D_2O$)
Singlet: 3.4 ppm, 8 protons.
Singlet: 3.1 ppm, 6 protons.
Singlet: 2.9 ppm, 3 protons.

EXAMPLE 6

Preparation of 1-methylsulfonia-4-oxacyclohexanechloride

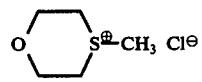 (6)

An aqueous solution of 1-methylsulfonia-4-oxacyclohexane iodide was filtered over a column containing an anion exchange resin charged with chloride ions. After evaporation of the eluate under reduced pressure 1-methylsulfonia-4-oxacyclohexane chloride was obtained in form of crystals of melting point 210° C (decomposition).

The active compounds according to the invention affect the physiological metabolism of plant growth and can therefore be used as plant-growth-regulators.

The diverse effects of the active compounds depend essentially on the point in time at which they are used, relative to the stage of development of the seed or of the plant, and on the concentrations used.

Plant-growth regulators are used for various purposes which are related to the stage of development of the plant.

The growth of the plants can be greatly inhibited by means of the compounds to be used according to the invention. Such inhibition of vegetative growth plays an important role in cereals since this can reduce or completely prevent falling over. At the same time, the compounds according to the invention achieve a strengthening of the stalk.

In the case of many crop plants, inhibition of the vegetative growth permits denser planting of the crop so that an increased yield relative to soil area can be achieved. A further mechanism of increasing the yield by means of growth inhibitors is based on the fact that the nutrients benefit blossoming and fruiting to an increased extent while vegetative growth is restricted.

However, a promotion of vegetative growth can also be achieved with the compounds according to the invention. This is of great value where it is the vegetative parts of the plants which are harvested. However, promotion of vegetative growth can at the same time also lead to promotion of generative growth so that, for example, more fruit or larger fruit, is formed.

Further, the active compounds according to the invention can be used to accelerate or retard the ripening of fruit and to improve the color of rruit. It is also possible to concentrate the ripening of the fruit within a shorter time. The desired effects can be achieved by varying the concentrations of the active compounds employed and by applying them at different times during the development of the plant.

The active compounds to be used according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphtahlenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin sulfite waste liquors and methyl cellulose.

The active compounds to be used according to the invention can be present in the formulations as a mixture with other active compounds.

The formulations in general contain from 0.1 to 95 percent by weight of active compound, preferably from 0.5 to 90 percent.

The active compounds can be used as such, as their formulations or as the application forms prepared therefrom, such as ready-to-use solutions, emulsions, foams, suspensions, powders, pastes and granules. They may be used in the customary manner, for example by watering, spraying, atomizing, scattering, dusting, treating of seeds, and the like.

The concentrations of active compound in the ready-to-use formulations can be varied within a fairly wide range. In general, concentrations from 0.0005 to 2%, preferably from 0.01 to 5%, by weight are used.

Furthermore, 0.1 to 100 kg, preferably 1 to 10 kg, of active compound are, in general, used per hectare of soil area.

The preferred period of time within which the growth regulators are used depends on the climatic and vegetative circumstances.

The present invention further provides methods to obtain plants whose growth has been regulated by their being grown in areas in which immediately prior to and/or during the time of the growing a compound of the formula (I) above was applied alone or in admixture with a diluent or carrier. It will be seen that the usual methods of providing a harvested crop may be improved by the present invention.

In the test Examples which follow, the activity as growth regulators of the compounds to be used according to the invention is illustrated, without excluding the possibility of further uses as growth regulators.

EXAMPLE A

Inhibition of growth/barley

Solvent: 10 parts by weight of methanol
Emulsifier: 2 parts by weight of polyethylene sorbitan monolaurate To prepare a suitable preparation of active compound, one part by weight of active compound was mixed with the stated amount of solvent and emulsifier and the mixture was made up to the desired concentration with water.

Young barley plants, 25–30 cm high, were sprayed with the preparation of active compound until dripping wet. After four weeks, the additional growth was measured and the inhibition of growth in % of the additional growth of the control plants was calculated. 100% means that growth had stopped and 0% denotes a growth corresponding to that of the untreated plants.

The active compounds, active-compound concentrations and results can be seen from Table A which follows.

Table A

Inhibition of growth/barley

| Active compound | Concentration in ppm | Inhibition of growth in % |
|---|---|---|
| Water (control) | — | 0 |
| Cl—CH$_2$—CH$_2$—N$^\oplus$(CH$_3$)$_3$ Cl$^\ominus$ (known) | 1,000 | 35 |
|  | 500 | 10 |
| H$_3$C\\$^\oplus$N⟨ring⟩S$^\oplus$-CH$_3$ 2 Cl$^\ominus$ (5) /H$_3$C | 1,000 | 50 |
|  | 500 | 35 |

Table A-continued

Inhibition of growth/barley

| Active compound | Concentration in ppm | Inhibition of growth in % |
|---|---|---|
| O⟨ring⟩S$^\oplus$-CH$_3$ Cl$^\ominus$ (6) | 500 | 30 |

EXAMPLE B

Inhibition of growth/wheat

Solvent: 10 parts by weight of methanol
Emulsifier: 2 parts by weight of polyethylene sorbitan monolaurate To prepare a suitable preparation of active compound, one part by weight of active compound was mixed with the stated amount of solvent and emulsifier and the mixture was made up to the desired concentration with water.

Young wheat plants, 25–30 cm high, were sprayed with the preparation of active compound until dripping wet. After four weeks, the additional growth was measured and the inhibition of growth in % of the additional growth of the control plants was calculated. 100% means that growth had stopped and 0% denoted a growth corresponding to that of the untreated plants.

The active compounds, active-compound concentrations and results can be seen from Table B which follows.

Table B

Inhibition of growth/wheat

| Active compound | Concentration in ppm | Inhibition of growth in % |
|---|---|---|
| Water (control) | — | 0 |
| Cl—CH$_2$—CH$_2$—N$^\oplus$(CH$_3$)$_3$ Cl$^\ominus$ (known) | 1,000 | 60 |
|  | 500 | 40 |
| (5) H$_3$C\\$^\oplus$N⟨ring⟩S$^\oplus$-CH$_3$ 2 Cl$^\ominus$ /H$_3$C | 1,000 | 80 |
|  | 500 | 60 |
| (6) O⟨ring⟩S$^\oplus$-CH$_3$ Cl$^\ominus$ | 500 | 40 |

EXAMPLE C

Promotion of growth/beans

Solvent: 10 parts by weight of methanol
Emulsifier: 2 parts by weight of polyethylene sorbitan monolaurate To prepare a suitable preparation of active compound, one part by weight of active compound was mixed with the stated amount of solvent and emulsifier and the mixture was made up to the desired concentration with water.

Young bean plants about 10 cm high were sprayed with the preparations of active compound until dripping wet. After fourteen days, the additional growth of the untreated plants was determined in comparison with the untreated control plants.

The active compounds, active-compound concentrations and results can be seen from Table C which follows.

Table C

Promotion of growth/beans

| Active compound | Concentration in ppm | Influence on growth in % of the control |
|---|---|---|
| Water (control) | — | 0 |
| (1) C₂H₅—⁺S⟨⟩S⁺—C₂H₅ 2 BF₄⁻ | 500 | +25 |
| (6) O⟨⟩S⁺—CH₃ Cl⁻ | 500 | +25 |

It will be understood that the specification and examples are illustrative but not limitative of the present invention and that other embodiments within the spirit and scope of the invention will suggest themselves to those skilled in the art.

What is claimed is:

1. Plant-growth regulant composition containing from 0.1 to 95% of a heterocyclic sulfonium salt of the formula

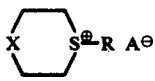 (I)

in which
R is methyl;
A⁻ is one equivalent of an anion of a chlorine or methyl sulfate; and
X is the group N+R'R"A⁻ in which
A⁻ is identified as above; and
R' and R", which may be identical or different, are each methyl; and at least one plant-growth regulatingly acceptable inert carrier.

2. Composition as claimed in claim 1 wherein A⁻ is a chlorine.

3. Composition as claimed in claim 1 wherein said heterocyclic sulfonium salt is 1-methylsulfonia-4-dimethylammonia-cyclohexane dimethosulfate.

4. Composition as claimed in claim 1 wherein said heterocyclic sulfonium salt is 1-methyl-sulfonia-4-dimethylammonia-cyclohexane dichloride.

5. Method of inhibiting the growth of plants which method comprises applying to the locus thereof an effective amount of a heterocyclic sulfonium salt of the formula

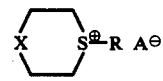 (I)

in which
R is methyl
A⁻ is one equivalent of an anion of a chlorine or methyl sulfate; and
X is the group N+R'R" A⁻ in which
A⁻ is identified as above;
R' and R", which may be identical or different, are each methyl.

6. Method as claimed in claim 5 wherein said salt is used at a dosage of from 0.1 to 100 kg per hectare of area of cultivation treated.

7. Method as claimed in claim 5 wherein said salt is used to inhibit the growth of barley plants.

8. Method as claimed in claim 5 wherein said salt is used to inhibit the growth of wheat plants.

9. Method according to claim 5 wherein A⁻ is methyl sulfate.

* * * * *

UNITED STATES PATENT AND TRADEMARK OFFICE
CERTIFICATE OF CORRECTION

PATENT NO. : 4,047,923
DATED : September 13, 1977
INVENTOR(S) : Klaus Naumann et al It is certified that error appears in the above-identified patent and that said Letters Patent are hereby corrected as shown below:

Title page, Inventors, "Lurssen" should read -- Lürssen --.
Title page, Ref. cited, Patent Number of Duerr "3,913,436" should read -- 3,813,436 --.
Column 2, line 13, "-$CH_2CH_2$-" should read -- -$CH_2$-$CH_2$- --.
Column 2, line 14, "flowing" should read -- following --.

Column 3, line 32, "Y-" should read -- $Y^{\ominus}$ --.
Column 3, line 41, "THe" should read -- The --.
Column 6, line 19, "rruit" should read -- fruit --.
Column 8, line 30, "denoted" should read -- denotes --.
Column 9, line 40, "chlorine" should read -- chloride --.
Column 10, line 7, "chlorine" should read -- chloride --.
Column 10, line 26, "chlorine" should read -- chloride --.

Signed and Sealed this

Sixteenth Day of May 1978

[SEAL]

Attest:

RUTH C. MASON
Attesting Officer

LUTRELLE F. PARKER
Acting Commissioner of Patents and Trademarks